(12) United States Patent
Thukral et al.

(10) Patent No.: US 9,330,302 B2
(45) Date of Patent: May 3, 2016

(54) POLARIZED GAZE TRACKING

(71) Applicant: MICROSOFT TECHNOLOGY LICENSING, LLC, Redmond, WA (US)

(72) Inventors: Vaibhav Thukral, Kirkland, WA (US); Sudipta Sinha, Redmond, WA (US); Vivek Pradeep, Snohomish, WA (US); Timothy Andrew Large, Bellevue, WA (US); Nigel Stuart Keam, Bellevue, WA (US); David Nister, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 219 days.

(21) Appl. No.: 14/191,305

(22) Filed: Feb. 26, 2014

(65) Prior Publication Data

US 2015/0242680 A1 Aug. 27, 2015

(51) Int. Cl.
*H04N 5/235* (2006.01)
*G06K 9/00* (2006.01)
(Continued)

(52) U.S. Cl.
CPC ............ *G06K 9/00335* (2013.01); *G06F 3/013* (2013.01); *G06K 9/00604* (2013.01); *G06K 9/2027* (2013.01); *H04N 5/2354* (2013.01); *H04N 5/23219* (2013.01)

(58) Field of Classification Search
CPC ............... G06F 3/013; G06K 9/00335; G06K 9/00604; G06K 9/2027; H04N 5/2354; H04N 5/23219

USPC .......................................................... 348/78
See application file for complete search history.

(56) References Cited

U.S. PATENT DOCUMENTS

| 5,345,281 A | 9/1994 | Taboada et al. |
| 7,428,320 B2 | 9/2008 | Northcott et al. |

(Continued)

FOREIGN PATENT DOCUMENTS

| EP | 0350957 B1 | 4/1996 |
| WO | 2010136762 A1 | 12/2010 |

OTHER PUBLICATIONS

Ebisawa, Y., "Improved Video-Based Eye-Gaze Detection Method", In Proceedings of the IEEE Transactions on Instrumentation and Measurement, vol. 47, Issue 4, Aug. 1998, 8 Pages.

(Continued)

*Primary Examiner* — David Harvey
(74) *Attorney, Agent, or Firm* — Dave Ream; Tom Wong; Micky Minhas

(57) ABSTRACT

Embodiments that relate to determining gaze locations are disclosed. In one embodiment a method includes shining light along an outbound light path to the eyes of the user wearing glasses. Upon detecting the glasses, the light is dynamically polarized in a polarization pattern that switches between a random polarization phase and a single polarization phase, wherein the random polarization phase includes a first polarization along an outbound light path and a second polarization orthogonal to the first polarization along a reflected light path. The single polarization phase has a single polarization. During the random polarization phases, glares reflected from the glasses are filtered out and pupil images are captured. Glint images are captured during the single polarization phase. Based on pupil characteristics and glint characteristics, gaze locations are repeatedly detected.

20 Claims, 7 Drawing Sheets

(51) Int. Cl.
*H04N 5/232* (2006.01)
*G06F 3/01* (2006.01)
*G06K 9/20* (2006.01)

(56) References Cited

U.S. PATENT DOCUMENTS

| | | | |
|---|---|---|---|
| 7,480,396 B2 | 1/2009 | Teiwes et al. | |
| 2002/0088927 A1 | 7/2002 | Simchoni | |
| 2002/0089744 A1 | 7/2002 | Myers | |
| 2006/0215076 A1 | 9/2006 | Karim | |
| 2008/0002863 A1 | 1/2008 | Northcott et al. | |
| 2010/0231699 A1 | 9/2010 | Jalbout et al. | |
| 2011/0170060 A1* | 7/2011 | Gordon | A61B 3/113 351/206 |
| 2011/0170061 A1 | 7/2011 | Gordon | |
| 2011/0279666 A1 | 11/2011 | Strombom et al. | |
| 2012/0218253 A1 | 8/2012 | Clavin | |
| 2013/0194401 A1 | 8/2013 | Bernard et al. | |
| 2013/0301004 A1 | 11/2013 | Kahn et al. | |
| 2013/0321265 A1* | 12/2013 | Bychkov | G06F 3/013 345/156 |

OTHER PUBLICATIONS

Bohme, M. et al., "Remote Eye Tracking: State of the Art and Directions for Future Development", In Proceedings of the 2nd Conference on Communication by Gaze Interaction—COGAIN 2006: Gazing Into the Future, Sep. 2006, 5 Pages.

ISA European Patent Office, International Search Report and Written Opinion issued in Application No. PCT/US2015/017001, Jun. 9, 2015, Netherlands, 10 pages.

Morimoto, C.H. et al.,"Pupil Detection and Tracking Using Multiple Light Sources", Journal of Image and Vision Computing, vol. 18, Issue 4, Mar. 2000, 5 pages.

Jo, H. et al., "A Robust Gaze Tracking Method for Users Wearing Glasses", Advanced Science and Technology Letters, vol. 43 (Multimedia 2013), Dec. 11, 2013, Korea, 4 pages.

IPEA European Patent Office, Second Written Opinion of the International Preliminary Examining Authority Issued in Application No. PCT/US2015/017001, Feb. 9, 2016, WIPO, 5 pages.

* cited by examiner

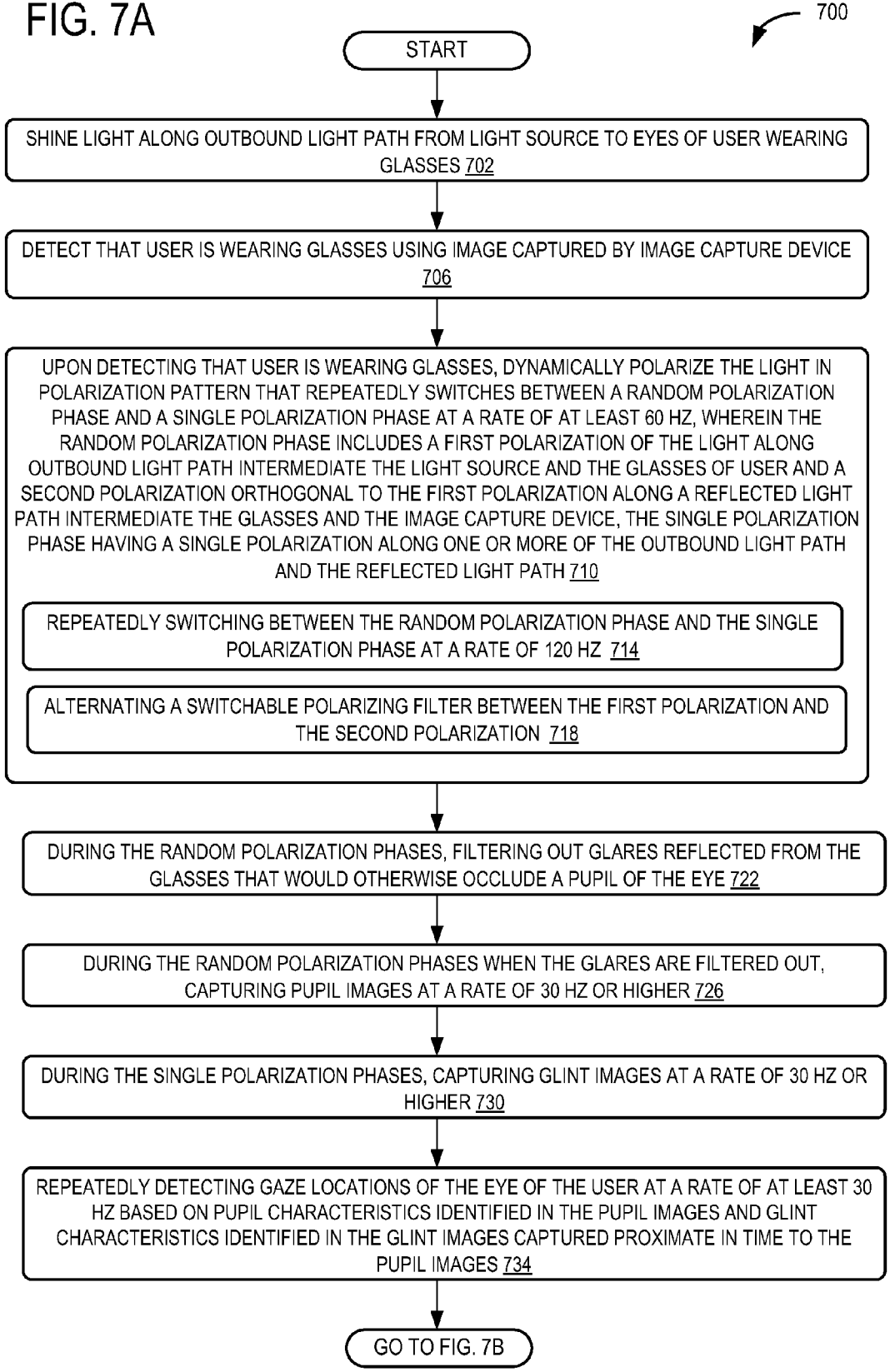

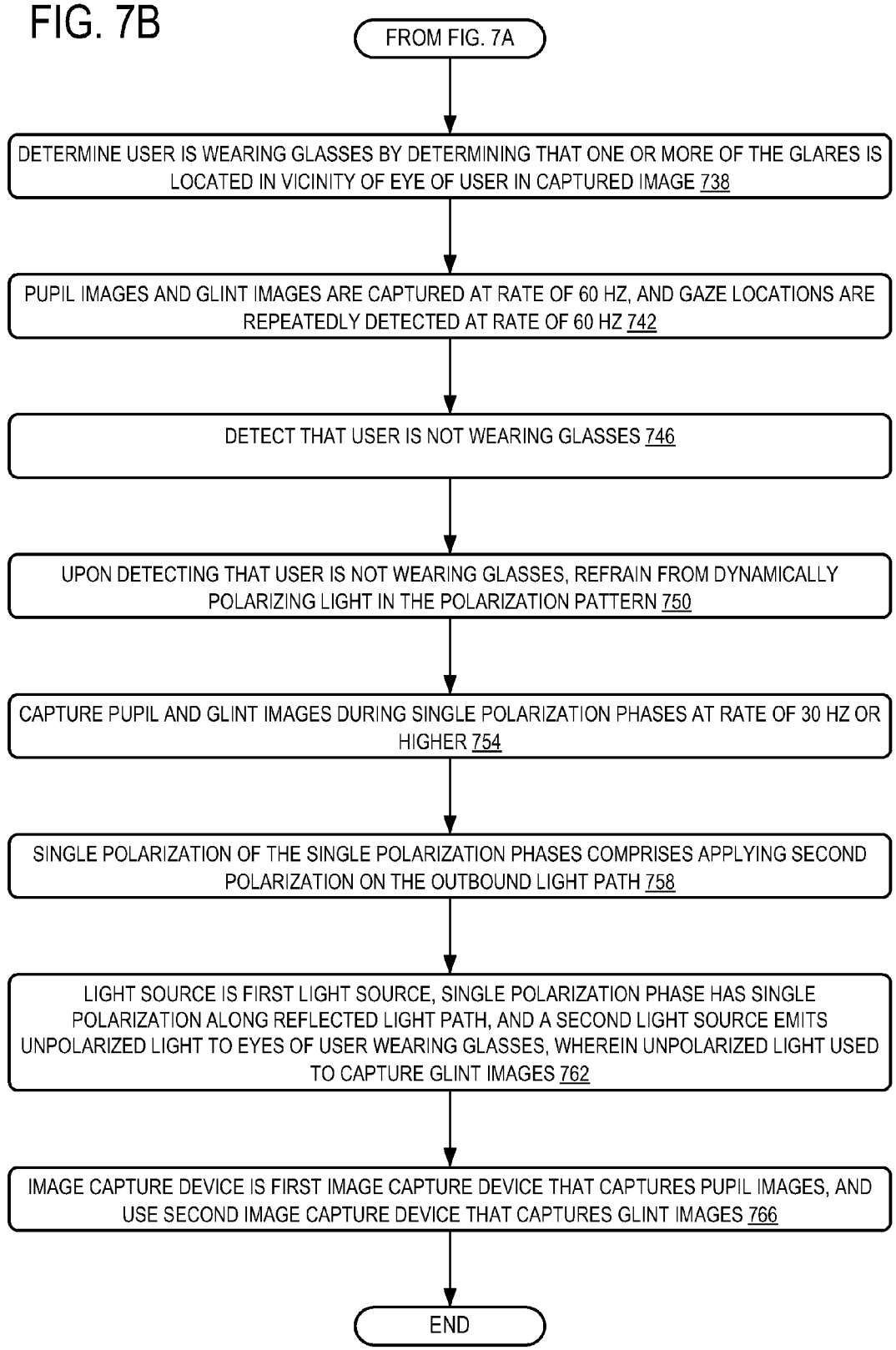

POLARIZED GAZE TRACKING

Eye or gaze tracking systems and techniques may be utilized to determine a direction and/or location of a person's gaze. In some examples, a light source may illuminate the eye or eyes of a user and a corresponding camera may capture images of the eye. Such images may include reflections from the cornea of the eye, or "glints." Positions of the pupil and glints from captured images may be utilized to determine a direction and/or location of a user's gaze in a surrounding environment.

However, in situations where a user is wearing glasses, light from the light source may cause specular reflections from a lens of the glasses. Such specular reflections may cause glares that can occlude corneal reflection glints and images of the pupil and/or limbus. Such glares may degrade the ability of a gaze tracking system to accurately determine positions of the pupil and/or glints. Accordingly, the accuracy of an estimated direction and/or location of a person's gaze may suffer.

SUMMARY

Various embodiments are disclosed herein that relate to systems and methods for determining gaze locations of an eye of a user. For example, one disclosed embodiment provides a method for determining gaze locations of an eye of a user in which light is shone along an outbound light path from a light source to the eyes of the user wearing glasses. The method includes detecting that the user is wearing glasses using an image captured by an image capture device.

Upon detecting that the user is wearing glasses, the light is dynamically polarized in a polarization pattern that repeatedly switches between a random polarization phase and a single polarization phase at a rate of at least 60 Hz, wherein the random polarization phase includes a first polarization of the light along the outbound light path intermediate the light source and the glasses of the user, and a second polarization orthogonal to the first polarization along a reflected light path intermediate the glasses and the image capture device. The single polarization phase has a single polarization along one or more of the outbound light path and the reflected light path.

During the random polarization phases, glares reflected from the glasses that would otherwise occlude a pupil of the eye are filtered out. During the random polarization phases when the glares are filtered out, pupil images are captured at a rate of 30 Hz or higher. During the single polarization phases, glint images are captured at a rate of 30 Hz or higher. Based on pupil characteristics identified in the pupil images and glint characteristics identified in the glint images captured proximate in time to the pupil images, the gaze locations are repeatedly detected at a rate of at least 30 Hz.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 7A and 7B are a flow chart of a method for determining gaze locations of a user according to an embodiment of the present disclosure.

DETAILED DESCRIPTION

Figure 1:
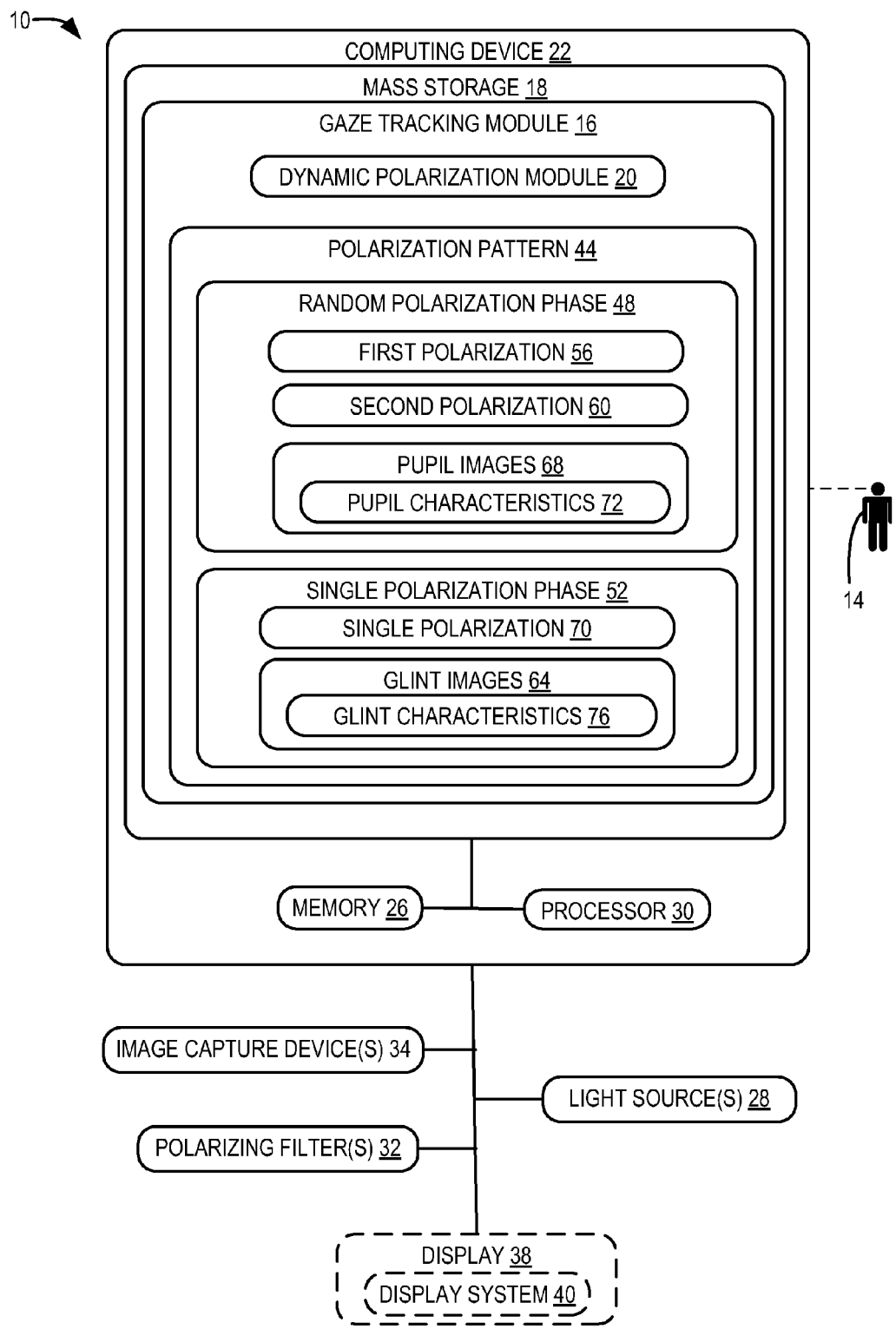
FIG. 1 is a schematic view of a gaze tracking system for determining gaze locations of an eye of a user according to an embodiment of the present disclosure.

FIG. 1 shows a schematic view of one embodiment of a gaze tracking system 10 for determining one or more gaze locations of an eye of a user 14. The gaze tracking system 10 includes a gaze tracking module 16 and dynamic polarization module 20 that may be stored in mass storage 18 of a computing device 22. The gaze tracking module 16 and dynamic polarization module 20 may be loaded into memory 26 and executed by a processor 30 of the computing device 22 to perform one or more of the methods and processes described in more detail below.

The gaze tracking system 10 includes one or more light sources 28 such as, for example, an LED light source. In some examples the light source(s) 28 may comprise infrared light sources that emit infrared light, such as an infrared LED. In other examples the light source(s) 28 may comprise visible light sources that emit visible light, such as a visible LED for camera flash purposes or keyboard illumination on a laptop computer. In some examples, the light source(s) 28 may comprise a display on a computing device, such as a mobile phone.

As described in more detail below, the light source 28 may shine light along an outbound light path to the eyes of a user who may be wearing glasses. One or more polarizing filters 32 are configured to dynamically polarize the light emitted by the light source 28. The gaze tracking system 10 further includes one or more image capture devices 34 that are configured to capture images of the light that is reflected and scattered from the glasses and the eye of the user.

Figure 2:
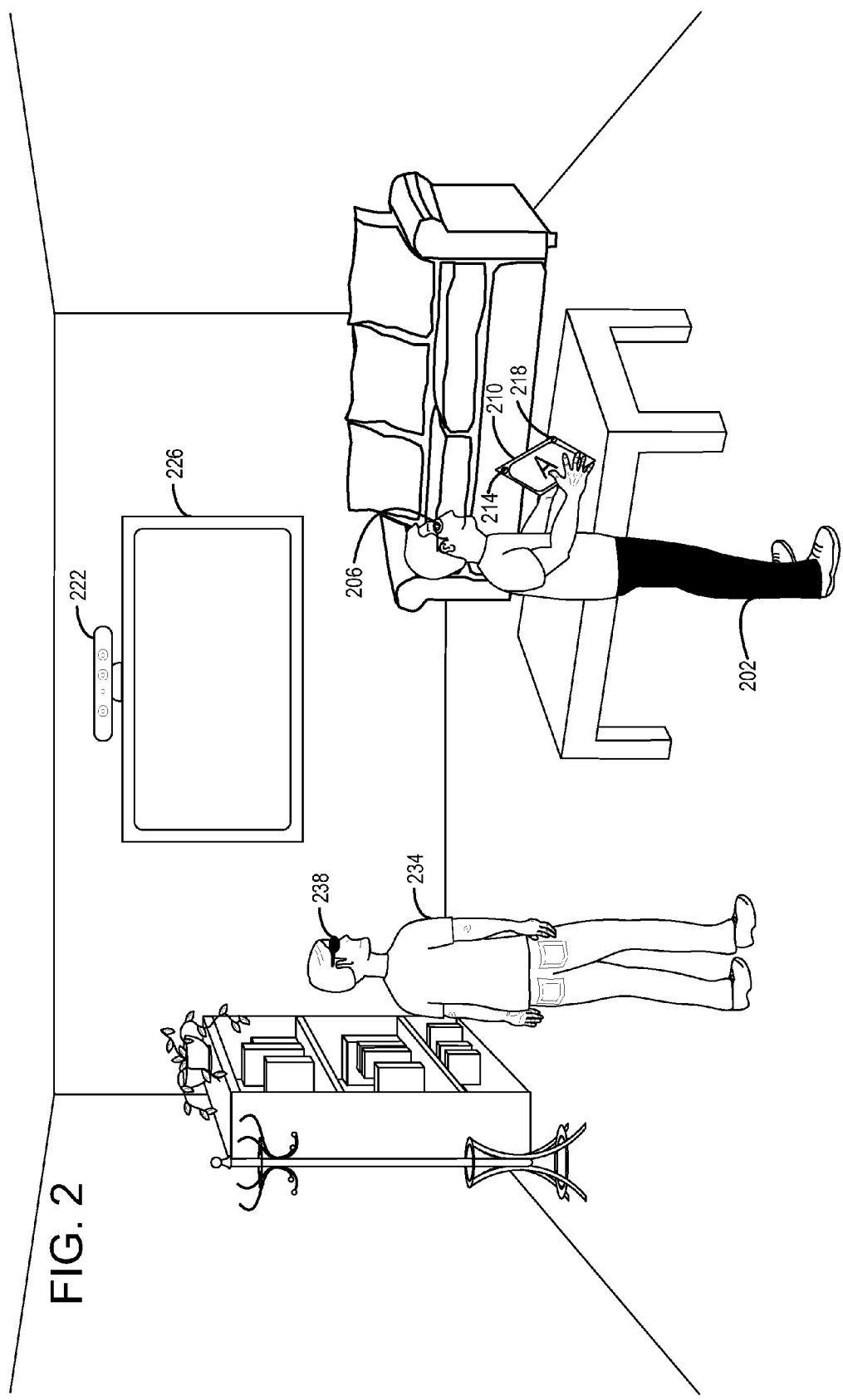
FIG. 2 a schematic perspective view of a room including two users wearing glasses, a wall-mounted display comprising a gaze tracking system and a tablet computer comprising a gaze tracking system according to an embodiment of the present disclosure.

In some examples, the computing device 22, light source(s) 28, polarizing filter(s) 32 and image capture device(s) 34 may be integrated into a common enclosure to form a single device. Such devices may include, but are not limited to, desktop computers, PCs, hand-held smart phones, e-readers, laptop, notebook and tablet computers, displays, interactive televisions, set-top boxes, gaming consoles, etc. For example and with reference to FIG. 2, a tablet user 202 wearing glasses 206 may utilize a tablet 210 that comprises gaze tracking system 10. The tablet 210 may include an LED light source 214 with a polarizing filter and a gaze detection camera 218.

In other examples, one or more of the light source(s) 28, polarizing filter(s) 32 and image capture device(s) 34 may be physically separate from and communicatively coupled to the computing device 22. In one example, the light source(s) 28, polarizing filter(s) 32 and image capture device(s) 34 may be located in an input device 222 mounted adjacent to a wall-mounted display 226, and may be communicatively coupled to a computing device 22 in the display or in a separate component, such as a gaming console, via a wired or wireless connection. A gaming user 234 wearing glasses 238 may use his eyes to interact with content displayed by the display 226 via the input device 222 and the gaze tracking module 16 on the computing device 22. It will be appreciated that many other types and configurations of gaze tracking systems 10 having various form factors, whether separate from or integrated with a computing device 22, may also be used and are within the scope of the present disclosure.

The computing device 22 may take the form of a desktop computing device, a mobile computing device such as a smart phone, laptop, notebook or tablet computer, network computer, home entertainment computer, interactive television, gaming system, or other suitable type of computing device. Additional details regarding the components and computing aspects of the computing device 22 are described in more detail below with reference to FIG. 8.

With reference again to FIG. 1 and as noted above, in some examples the gaze tracking system 10 may include or be communicatively coupled to a display device 38. In one example, the display device 38 may comprise a separate display, such as a standalone monitor for example, that is operatively connected to computing device 22 via a wired or wireless connection. The display 38 may include a display system 40 for presenting one or more visual elements to a user.

The gaze tracking module 16 may be configured to determine gaze directions of one or both of a user's eyes in any suitable manner. For example, the gaze tracking module 16 may utilize images of the pupil and corneal reflections that generate corneal glints captured by the image capture device(s) 34 to determine a center of the pupil and locations of the glints. A vector between the glints and the pupil center may be used to determine the gaze location of the eye.

In one example a bright pupil technique may be utilized in which the illuminated light from the light source(s) 28 is coaxial with the optical path of the eye, causing the light to reflect off the retina. In other examples, a dark pupil technique may be utilized in which the illuminated light is offset from the optical path. For purposes of the present disclosure, examples of the gaze tracking system 10 utilizing a dark pupil technique will be provided.

Images of the corneal glints and of the pupils as determined from image data gathered from the image capture device(s) 34 may be used to determine an optical axis of each eye. Using this information, the gaze tracking module 16 may determine a direction and/or at what physical object or virtual object the user is gazing. The gaze tracking module 16 may further determine at what point on a physical or virtual object the user is gazing. Such gaze tracking data may then be provided to the computing device 22, and may be utilized by one or more applications or other programs as needed.

With reference now also to FIGS. 3-6, descriptions of example embodiments of the gaze tracking system 10 will now be provided. In one example shown in FIG. 3, the gaze tracking system 10 includes a first infrared light source 302 that shines infrared light along a first outbound light path 306, and a second infrared light source 310 that shines infrared light along a second outbound light path 314. It will be appreciated that the first outbound light path 306 extends from the first light source 302 to the eye 322 and the second outbound light path 314 extends from the second light source 310 to the eye. It will be appreciated that infrared light sources are provided merely as examples, and that any other suitable light sources may be utilized and are within the scope of the present disclosure. With reference also to FIG. 1 and as described in more detail below, upon detecting that the user 14 is wearing glasses, the infrared light emitted from the first light source 302 and second light source 310 may be dynamically polarized, using an outbound polarizing filter 318 and an inbound polarizing filter 340, in a polarization pattern 44 that repeatedly switches between a random polarization phase 48 and a single polarization phase 52.

Figure 3:
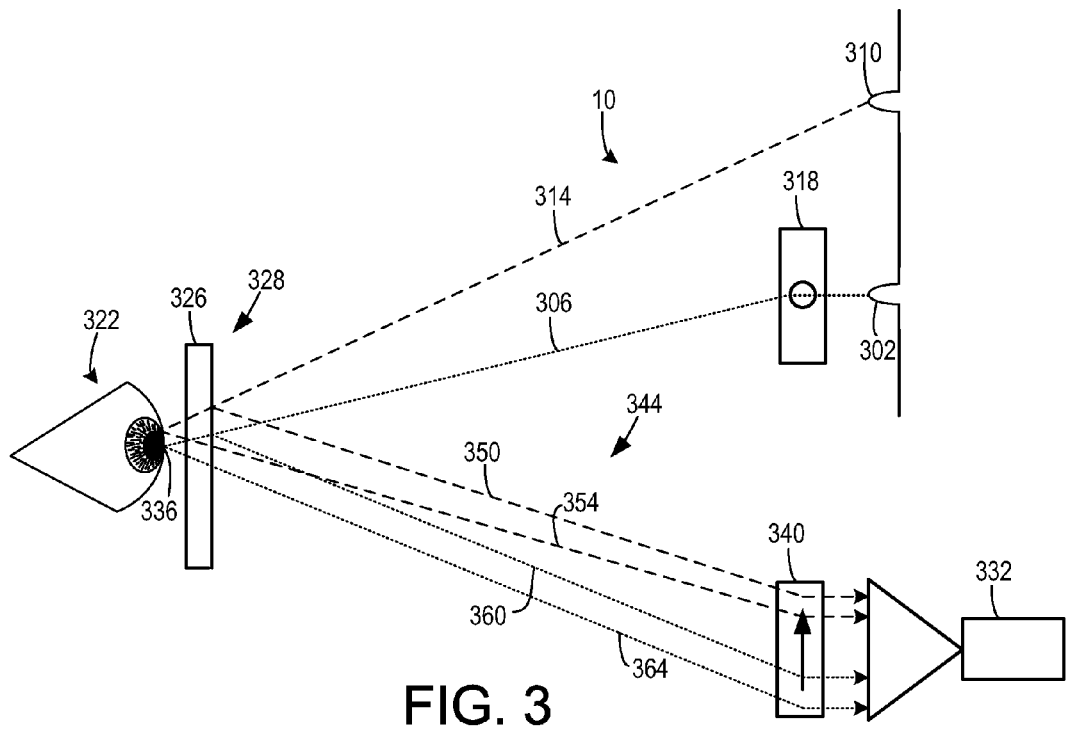
FIG. 3 is a schematic view of a gaze tracking system according to an embodiment of the present disclosure.

As shown in FIG. 3, an eye 322 of user 14 peers through a lens 326 of glasses 328 worn by the user. An image capture device 332 is configured to capture images of light emitted by the first light source 302 and second light source 310 that is reflected and scattered from the eye 322 and the lens 326 of glasses 328. As noted above, light from light sources 302 and/or 310 may reflect from lens 326 to cause glares in the images captured by the image capture device 332. Advantageously, the dynamic polarization module 20 is configured to substantially filter out such glares that may otherwise occlude the pupil 336 of the eye 322.

More particularly and in one example, the dynamic polarization module 20 is configured to dynamically polarize the infrared light emitted from the first light source 302 and second light source 310, via outbound polarizing filter 318 and inbound polarizing filter 340, in a polarization pattern 44 that repeatedly switches between a random polarization phase 48 and a single polarization phase 52 at a rate of at least 60 Hz. The random polarization phase 48 includes a first polarization 56 of the infrared light, provided by the outbound polarizing filter 318, along the first outbound light path 306 intermediate the first light source 302 and the glasses 328 of the user. The random polarization phase 48 also includes a second polarization 60 that is orthogonal to the first polarization 56, and is provided by an inbound polarizing filter 340, along a reflected light path 344 intermediate the glasses 328 and the image capture device 332. In this example the single polarization phase 52 has a single polarization 70 provided by the inbound polarizing filter 340 along the reflected light path 344. It will be appreciated that the reflected light path 344 extends from the eye 322 to the image capture device 332.

As shown in FIG. 3, a first portion 350 of unpolarized light from the second outbound light path 314 is reflected off the lens 326 along the reflected light path 344 through the outbound polarizing filter 340 to the image capture device 332. A second portion 354 of unpolarized light from the second outbound light path 314 passes through lens 326 and is reflected off the cornea of the eye 322, creating corneal glints that travel along the reflected light path 344 through the inbound polarizing filter 340 to the image capture device 332. During the single polarization phase 52, the first portion 350 and second portion 354 of light may be used to capture glint images 64.

The outbound polarizing filter 318 and inbound polarizing filter 340 may comprise linear, circular or any other suitable type of polarizing filters. As shown in FIG. 3, the first outbound light path 306 includes light that has passed through horizontal polarizing filter 318. A first portion 360 of the horizontally polarized light from the first outbound light path 306 is reflected off the lens 326 along the reflected light path 344 through the vertically polarized inbound polarizing filter 340 to the image capture device 332. This first portion 360 of light includes glares reflected from the surface of lens 326. Because it is reflected, this first portion 360 of light maintains its horizontal polarization, which is orthogonal to the vertical polarization of the inbound polarizing filter 340. Accordingly, the inbound polarizing filter 340 substantially attenuates and cancels the glares from this first portion 360 of light before it reaches the image capture device 332. It will be appreciated that the orientations of the outbound polarizing filter 318 and the inbound polarizing filter 340 may have any suitable orientations that are orthogonal to one another.

A second portion 364 of light from the first outbound light path 306 passes through lens 326 and is reflected off the cornea of the eye 322, creating horizontally polarized corneal glints. The horizontally polarized corneal glints in this second portion 364 travel along the reflected light path 344 through the vertically polarized inbound polarizing filter 340 to the image capture device 332. Because it is reflected, this second portion 364 of light also maintains its horizontal polarization. Accordingly, the vertically polarized inbound polarizing filter 340 substantially attenuates and cancels the horizontally polarized corneal glints from this second portion 364 of light before it reaches the image capture device 332.

This second portion 364 of light is also scattered by the pupil 336, creating unpolarized diffuse light that illuminates the pupil and limbus features. This unpolarized diffuse light from the pupil 336 also travels along light path 344 through the inbound polarizing filter 340 to the image capture device 332. Advantageously, by attenuating the glares and glints from the first portion 360 and second portion 364 of light from the first outbound light path 306 as described above, during the random polarization phase 48 the unpolarized diffuse light in the second portion 364 may be used to capture pupil images 68 that are not occluded by such glares and/or glints.

As noted above, the dynamic polarization module 20 is configured to dynamically polarize the infrared light in a polarization pattern 44 that repeatedly switches between the random polarization phase 48 and single polarization phase 52 at a rate of at least 60 Hz. In some examples during the single polarization phases 52, glint images 64 may be captured at a rate of 30 Hz or higher. During the random polarization phases 48 when the glares are filtered out, pupil images 68 may also be captured at a rate of 30 Hz or higher. Advantageously, using these glint images 64 and pupil images 68, gaze locations of the eye 322 may be repeatedly detected at a rate of at least 30 Hz based on pupil characteristics 72 identified in the pupil images and glint characteristics 76 identified in the glint images captured proximate in time to the pupil images. For example, where pupil images 68 and glint images 64 are captured at a rate of 30 Hz., an interval between an adjacent captured pupil image and glint image may be 0.020 secs, 0.015 secs, 0.010 secs, or any other suitable interval.

Such pupil characteristics 72 may include, but are not limited to, a center of the pupil. Such glint characteristics 76 may include, but are not limited to, locations of the glints relative to the pupil center. As noted above, any suitable gaze-tracking technique may be utilized to determine such gaze locations.

In some examples, such as particular applications or programs that may receive more frequent eye movements from a user, faster capture rates and more frequent gaze location detections may be utilized. For example, the dynamic polarization module may be configured to repeatedly switch between the random polarization phase 48 and the single polarization phase 52 at a rate of between 60 Hz and 120 Hz. In such examples the pupil images 68 and glint images 64 may be captured at a rate of between 30 Hz. and 60 Hz.

In one example, the rate of switching between the random polarization phase 48 and the single polarization phase 52 may be twice the rate of capturing pupil images 68, and twice the rate of capturing glint image 64. For example, the dynamic polarization module may be configured to repeatedly switch between the random polarization phase 48 and the single polarization phase 52 at a rate of 120 Hz. and the pupil images 68 and glint images 64 may be captured at a rate of 60 Hz.

In some examples, the dynamic polarization module 20 may be configured to detect whether the user is wearing glasses. For example, the dynamic polarization module 20 may identify glares from glasses by determining that one or more glares are located in the vicinity of an eye of a user.

The dynamic polarization module 20 may also distinguish such glares from corneal glints. Glares reflected from a lens of glasses are typically much larger in size than a corneal glint. Glares may also have a distinctive, irregular shape. On the other hand, corneal glints are typically smaller than glares, often include multiple radiating arms, and may be circular with a diameter approximately twice the diameter of the pupil. In some examples, the dynamic polarization module may use such distinguishing information to identify one or more glares from glasses.

In some examples, the dynamic polarization module 20 may detect that the user is not wearing glasses. In this situation, glares from glasses are not present. Accordingly, upon detecting that the user is not wearing glasses, the dynamic polarization module 20 may be configured to refrain from dynamically polarizing the infrared light in the polarization pattern 44. Advantageously, this may enable the gaze tracking system 10 to reduce power consumption by, for example, performing gaze tracking by illuminating the second, unpolarized light source 310 and not the first, polarized light source 302. In one example and using light from the second light source 310, pupil images 68 and glint images 64 may be captured during the single polarization phases 52 at a rate of 30 Hz., and the gaze locations may also be detected at a rate of 30 Hz.

Figure 4:
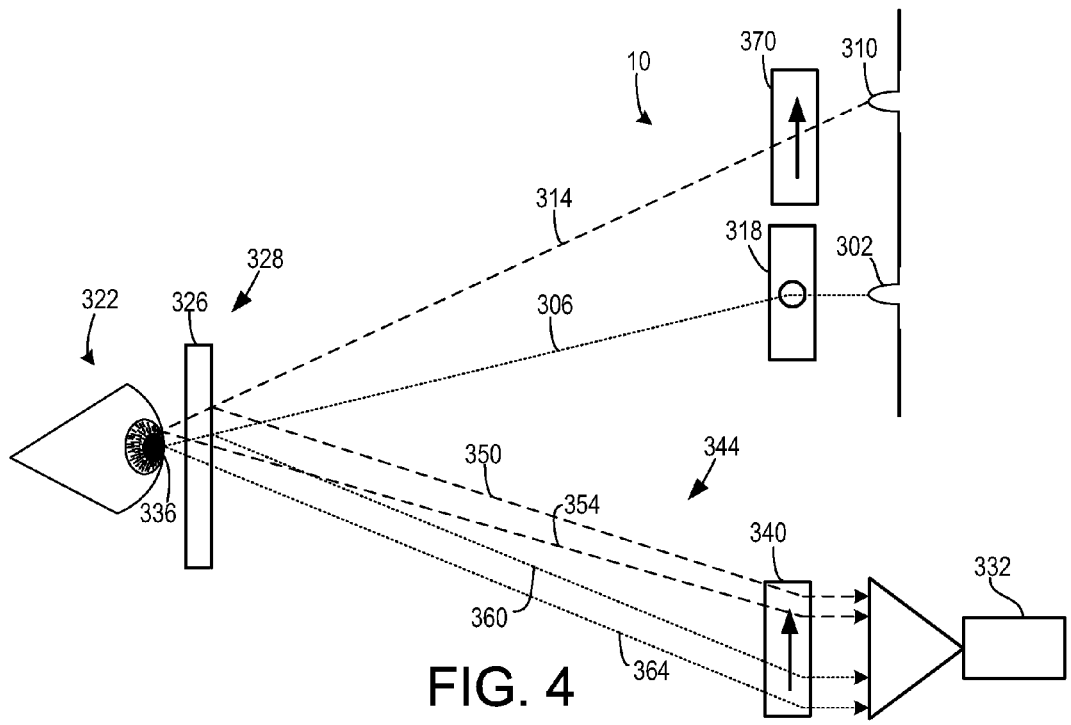
FIG. 4 is a schematic view of a gaze tracking system according to another embodiment of the present disclosure.

With reference now to FIG. 4, in another example an additional outbound polarizing filter 370 may be added to the second light source 310, where the filter 370 has the same orientation as the inbound polarizing filter 340. With this configuration, the light traveling along both the first outbound light path 306 and the second outbound light path 314 is polarized. Advantageously, the outbound polarizing filter 318 and the additional outbound polarizing filter 370 may be configured to cause the light traveling along the first outbound light path 306 and the second outbound light path 314 to have a similar luminance. In this manner, glint images 64 and pupil images 68 captured at the image capture device 332 may have a similar luminance and signal-to-noise ratio, which may enhance an accuracy of the gaze location determinations.

Figure 5:
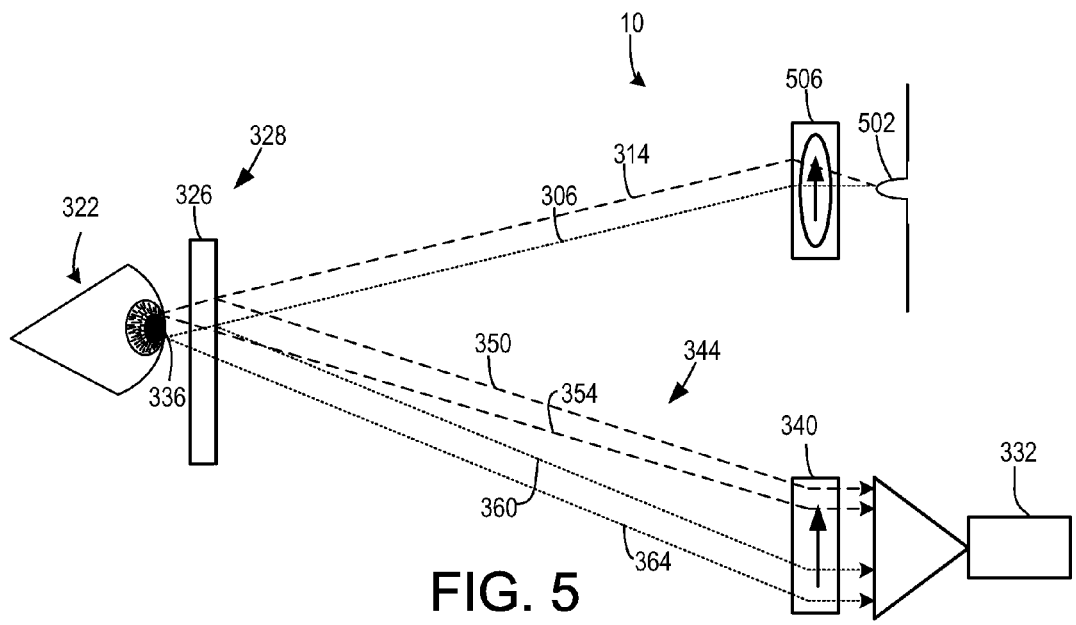
FIG. 5 is a schematic view of a gaze tracking system according to another embodiment of the present disclosure.

With reference now to FIG. 5, in another example the gaze tracking system 10 may comprise a single infrared light source 502 and a switchable polarizing filter 506 that may alternate between a first polarization and a second polarization that is orthogonal to the first polarization. In the example of FIG. 5, the switchable polarizing filter 506 may alternate between vertical and horizontal orientations. Accordingly, infrared light emitted from the single light source 502 may be dynamically polarized in a polarization pattern 44 as described above, and captured by the image capture device 332. Glint images 64 and pupil images 68 as described above may then be captured and utilized for determining gaze locations as described above.

Figure 6:
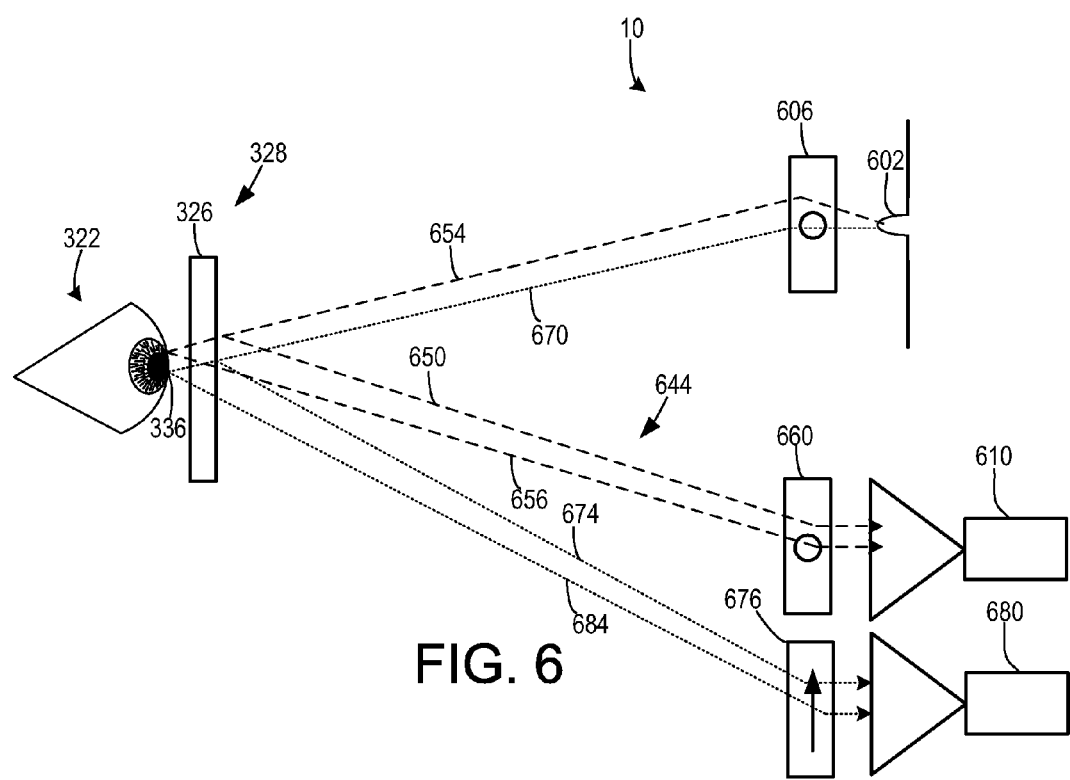
FIG. 6 is a schematic view of a gaze tracking system according to another embodiment of the present disclosure

With reference now to FIG. 6, in another example the gaze tracking system 10 may comprise a single infrared light source 602 and a single outbound polarizing filter 606 that polarizes light emitted from the light source in a first orientation. In this example, a first portion 650 of polarized light from a first outbound light path 654 is reflected off the lens 326 along the reflected light path 644 through a first inbound polarizing filter 660 to a first image capture device 610. As shown in FIG. 6, the first inbound polarizing filter 660 has the same horizontal orientation as the outbound polarizing filter 606.

Similarly, a second portion 656 of polarized light from the first outbound light path 654 passes through lens 326 and is reflected off the cornea of the eye 322, creating corneal glints that travel along the reflected light path 644 through the first inbound polarizing filter 660 to the first image capture device 610. As explained above, during the single polarization phase 52, the first portion 650 and second portion 656 of light may be used to capture glint images 64 with the first image capture device 610.

As shown in FIG. 6, second outbound light path 670 includes light that has passed through outbound polarizing filter 606. A first portion 674 of the polarized light from the second outbound light path 670 is reflected off the lens 326 along the reflected light path 644 through a second inbound polarizing filter 676 to a second image capture device 680. The second inbound polarizing filter 676 has a vertical orientation orthogonal to the horizontal orientation of the outbound polarizing filter 606. Accordingly, the second inbound polarizing filter 676 substantially attenuates and cancels the glares from this first portion 674 of light before it reaches the second image capture device 680.

A second portion 684 of light from the second outbound light path 670 passes through lens 326 and is reflected off the cornea of the eye 322, creating horizontally polarized corneal glints. These polarized glints in second portion 684 travel along the reflected light path 644 through the vertically polarized second inbound polarizing filter 676 to the second image capture device 680. Accordingly, the second inbound polarizing filter 676 substantially attenuates and cancels the horizontally polarized corneal glints from this second portion 684 of light before it reaches the second image capture device 680. As explained above, during the random polarization phase 48 the first portion 674 and second portion 684 of light may be used to capture pupil images 68 with the second image capture device 680.

FIGS. 7A and 7B illustrate a flow chart of a method 700 for navigating a hierarchy of visual elements according to an embodiment of the present disclosure. The following description of method 700 is provided with reference to the software and hardware components of the gaze tracking system 10 described above and shown in FIGS. 1-6. It will be appreciated that method 700 may also be performed in other contexts using other suitable hardware and software components.

With reference to FIG. 7A, at 702 the method 700 may include shining light along an outbound light path from a light source to the eyes of the user wearing glasses. At 706 the method 700 includes detecting that the user is wearing glasses using an image captured by an image capture device. At 710 the method 700 may include, upon detecting that the user is wearing glasses, dynamically polarizing the light in a polarization pattern that repeatedly switches between a random polarization phase and a single polarization phase at a rate of at least 60 Hz. The random polarization phase includes a first polarization of the light along the outbound light path intermediate the light source and the glasses of the user and a second polarization orthogonal to the first polarization along a reflected light path intermediate the glasses and the image capture device. The single polarization phase has a single polarization along one or more of the outbound light path and the reflected light path.

At 714 the method 700 may include dynamically polarizing the light in a polarization pattern by repeatedly switching between the random polarization phase and the single polarization phase at a rate of 120 Hz. At 718 the method 700 may include dynamically polarizing the light by alternating a switchable polarizing filter between the first polarization and the second polarization orthogonal to the first polarization. At 722 the method 700 may include, during the random polarization phases, filtering out glares reflected from the glasses that would otherwise occlude a pupil of the eye.

At 726 the method 700 may include during the random polarization phases when the glares are filtered out, capturing pupil images at a rate of 30 Hz or higher. At 730 the method 700 may include, during the single polarization phases, capturing glint images at a rate of 30 Hz or higher. At 734 the method 700 may include repeatedly detecting the gaze locations at a rate of at least 30 Hz based on pupil characteristics identified in the pupil images and glint characteristics identified in the glint images captured proximate in time to the pupil images.

With reference now to FIG. 7B, at 738 the method 700 may include detecting that the user is wearing glasses by determining that one or more of the glares is located in the vicinity of the eye of the user in the captured image. At 742 the method 700 may include capturing the pupil images and the glint images at a rate of 60 Hz., and repeatedly detecting the gaze locations at a rate of 60 Hz. At 746 the method 700 may include detecting that the user is not wearing glasses. At 750 the method 700 may include, upon detecting that the user is not wearing glasses, refraining from dynamically polarizing the light in the polarization pattern.

At 754 the method 700 may include capturing the pupil images and the glint images during the single polarization phases at a rate of 30 Hz or higher. At 758 the method 700 may include the single polarization of the single polarization phases comprising applying the second polarization on the outbound light path. At 762, where the light source is a first light source, the method 700 may include a second light source emitting unpolarized light to the eyes of the user wearing glasses, wherein the unpolarized light is used to capture the glint images. At 766, wherein the image capture device is a first image capture device that captures the pupil images, the method 700 may include using a second image capture device that captures the glint images.

It will be appreciated that method 700 is provided by way of example and is not meant to be limiting. Therefore, it is to be understood that method 700 may include additional and/or alternative steps than those illustrated in FIGS. 7A and 7B. Further, it is to be understood that method 700 may be performed in any suitable order. Further still, it is to be understood that one or more steps may be omitted from method 700 without departing from the scope of this disclosure.

Figure 8:
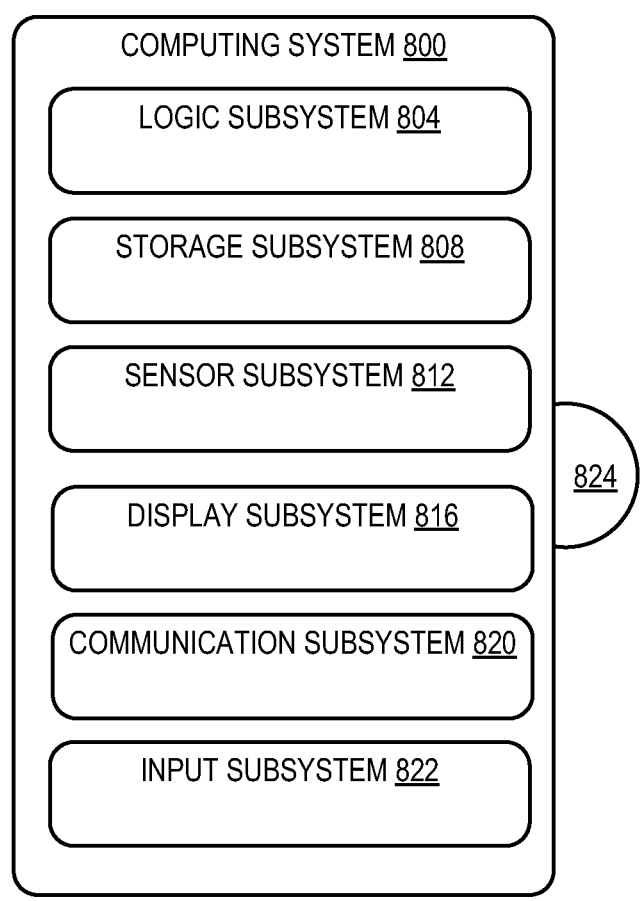
FIG. 8 is a simplified schematic illustration of an embodiment of a computing device.

FIG. 8 schematically shows a nonlimiting embodiment of a computing system 800 that may perform one or more of the above described methods and processes. Computing device 22 may take the form of or include one or more aspects of computing system 800. Computing system 800 is shown in simplified form. It is to be understood that virtually any computer architecture may be used without departing from the scope of this disclosure. In different embodiments, computing system 800 may take the form of a mainframe computer, server computer, desktop computer, laptop computer, tablet computer, home entertainment computer, network computing device, mobile computing device, mobile communication device, gaming device, etc.

As shown in FIG. 8, computing system 800 includes a logic subsystem 804, storage subsystem 808, and sensor subsystem 812. Computing system 800 may optionally include a display subsystem 816, communication subsystem 820, input subsystem 822 and/or other subsystems and components not shown in FIG. 8. Computing system 800 may also include computer readable media, with the computer readable media including computer readable storage media and computer readable communication media. Computing system 800 may also optionally include other user input devices such as keyboards, mice, game controllers, and/or touch screens, for example. Further, in some embodiments the methods and processes described herein may be implemented as a computer application, computer service, computer API, computer library, and/or other computer program product in a computing system that includes one or more computers.

Logic subsystem 804 may include one or more physical devices configured to execute one or more instructions. For example, the logic subsystem 804 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem 804 may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Storage subsystem 808 may include one or more physical, persistent devices configured to hold data and/or instructions executable by the logic subsystem 804 to implement the herein described methods and processes. When such methods and processes are implemented, the state of storage subsystem 808 may be transformed (e.g., to hold different data).

Storage subsystem 808 may include removable media and/or built-in devices. Storage subsystem 808 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Storage subsystem 808 may include devices with one or more of the following characteristics: volatile, nonvolatile, dynamic, static, read/write, read-only, random access, sequential access, location addressable, file addressable, and content addressable.

In some embodiments, aspects of logic subsystem 804 and storage subsystem 808 may be integrated into one or more common devices through which the functionally described herein may be enacted, at least in part. Such hardware-logic components may include field-programmable gate arrays (FPGAs), program- and application-specific integrated circuits (PASIC/ASICs), program- and application-specific standard products (PSSP/ASSPs), system-on-a-chip (SOC) systems, and complex programmable logic devices (CPLDs), for example.

FIG. 8 also shows an aspect of the storage subsystem 808 in the form of removable computer readable storage media 824, which may be used to store data and/or instructions executable to implement the methods and processes described herein. Removable computer-readable storage media 824 may take the form of CDs, DVDs, HD-DVDs, Blu-Ray Discs, EEPROMs, and/or floppy disks, among others.

It is to be appreciated that storage subsystem 808 includes one or more physical, persistent devices. In contrast, in some embodiments aspects of the instructions described herein may be propagated in a transitory fashion by a pure signal (e.g., an electromagnetic signal, an optical signal, etc.) that is not held by a physical device for at least a finite duration. Furthermore, data and/or other forms of information pertaining to the present disclosure may be propagated by a pure signal via computer-readable communication media.

Sensor subsystem 812 may include one or more sensors configured to sense different physical phenomenon (e.g., visible light, infrared light, sound, acceleration, orientation, position, etc.) as described above. Sensor subsystem 812 may be configured to provide sensor data to logic subsystem 804, for example. such data may include image information, ambient lighting information, depth information, audio information, position information, motion information, user location information, and/or any other suitable sensor data that may be used to perform the methods and processes described above.

When included, display subsystem 816 may be used to present a visual representation of data held by storage subsystem 808. As the above described methods and processes change the data held by the storage subsystem 808, and thus transform the state of the storage subsystem, the state of the display subsystem 816 may likewise be transformed to visually represent changes in the underlying data. The display subsystem 816 may include one or more display devices utilizing virtually any type of technology. Such display devices may be combined with logic subsystem 804 and/or storage subsystem 808 in a shared enclosure, or such display devices may be peripheral display devices.

When included, communication subsystem 820 may be configured to communicatively couple computing system 800 with one or more networks and/or one or more other computing devices. Communication subsystem 820 may include wired and/or wireless communication devices compatible with one or more different communication protocols. As nonlimiting examples, the communication subsystem 820 may be configured for communication via a wireless telephone network, a wireless local area network, a wired local area network, a wireless wide area network, a wired wide area network, etc. In some embodiments, the communication subsystem may allow computing system 800 to send and/or receive messages to and/or from other devices via a network such as the Internet.

When included, input subsystem 822 may comprise or interface with one or more sensors or user-input devices such as a game controller, gesture input detection device, voice recognizer, inertial measurement unit, keyboard, mouse, or touch screen. In some embodiments, the input subsystem 822 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

The term "module" may be used to describe an aspect of the gaze tracking system 10 that is implemented to perform one or more particular functions. In some cases, such a module may be instantiated via logic subsystem 804 executing instructions held by storage subsystem 808. It is to be understood that different modules may be instantiated from the same application, service, code block, object, library, routine, API, function, etc. Likewise, the same module may be instantiated by different applications, services, code blocks, objects, routines, APIs, functions, etc. The term "module" is meant to encompass individual or groups of executable files, data files, libraries, drivers, scripts, database records, etc.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method for determining gaze locations of an eye of a user, the method comprising:
    shining light along an outbound light path from a light source to the eyes of the user wearing glasses;
    detecting that the user is wearing glasses using an image captured by an image capture device;
    upon detecting that the user is wearing glasses, dynamically polarizing the light in a polarization pattern that repeatedly switches between a random polarization phase and a single polarization phase at a rate of at least 60 Hz, wherein the random polarization phase includes a first polarization of the light along the outbound light path intermediate the light source and the glasses of the user and a second polarization orthogonal to the first polarization along a reflected light path intermediate the glasses and the image capture device, and the single polarization phase having a single polarization along one or more of the outbound light path and the reflected light path;
    during the random polarization phases, filtering out glares reflected from the glasses that would otherwise occlude a pupil of the eye;
    during the random polarization phases when the glares are filtered out, capturing pupil images at a rate of 30 Hz or higher;
    during the single polarization phases, capturing glint images at a rate of 30 Hz or higher; and
    repeatedly detecting the gaze locations at a rate of at least 30 Hz based on pupil characteristics identified in the pupil images and glint characteristics identified in the glint images captured proximate in time to the pupil images.

2. The method of claim 1, wherein detecting that the user is wearing glasses further comprises determining that one or more of the glares is located in the vicinity of the eye of the user in the captured image.

3. The method of claim 1, wherein dynamically polarizing the light in a polarization pattern further comprises repeatedly switching between the random polarization phase and the single polarization phase at a rate of 120 Hz.

4. The method of claim 1, wherein the pupil images and the glint images are captured at a rate of 60 Hz., and the gaze locations are repeatedly detected at a rate of 60 Hz.

5. The method of claim 1, further comprising:
    detecting that the user is not wearing glasses;
    upon detecting that the user is not wearing glasses, refraining from dynamically polarizing the light in the polarization pattern that repeatedly switches between the random polarization phase and the single polarization phase; and
    capturing the pupil images and the glint images during the single polarization phases at a rate of 30 Hz or higher.

6. The method of claim 1, wherein the single polarization of the single polarization phases further comprises applying the second polarization on the outbound light path.

7. The method of claim 1, wherein dynamically polarizing the light comprises alternating a switchable polarizing filter between the first polarization and the second polarization orthogonal to the first polarization.

8. The method of claim 1, wherein the light source is a first light source, and a second light source emits unpolarized light to the eyes of the user wearing glasses, wherein the unpolarized light is used to capture the glint images.

9. The method of claim 1, wherein the image capture device is a first image capture device that captures the pupil images, and the method further comprises using a second image capture device that captures the glint images.

10. A gaze tracking system for determining gaze locations of an eye of a user, the gaze tracking system comprising:
    a light source for shining light along an outbound light path to the eyes of the user wearing glasses;
    a polarizing filter configured to dynamically polarize the light;
    an image capture device configured to capture images of the light reflected and scattered from the eye of the user and the glasses;
    a computing device operatively connected to at least the light source and the image capture device;
    a dynamic polarization module executed by a processor of the computing device, the dynamic polarization module configured to:
        detect that the user is wearing glasses using an image captured by the image capture device;
        upon detecting that the user is wearing glasses, dynamically polarize the light in a polarization pattern that repeatedly switches between a random polarization phase and a single polarization phase at a rate of at least 60 Hz, wherein the random polarization phase includes a first polarization of the light along the outbound light path intermediate the light source and the glasses of the user and a second polarization orthogonal to the first polarization along a reflected light path intermediate the glasses and the image capture device, and the single polarization phase having a single polarization along one or more of the outbound light path and the reflected light path;
        during the random polarization phases, filter out glares reflected from the glasses that would otherwise occlude a pupil of the eye;
        during the random polarization phases when the glares are filtered out, capture pupil images with the image capture device at a rate of 30 Hz or higher; and
        during the single polarization phases, capture glint images with the image capture device at a rate of 30 Hz or higher; and
    a gaze tracking module configured to repeatedly detect the gaze locations at a rate of at least 30 Hz based on pupil characteristics identified in the pupil images and glint characteristics identified in the glint images captured proximate in time to the pupil images.

11. The gaze tracking system of claim 10, wherein the dynamic polarization module is further configured to detect that the user is wearing glasses by determining that one or more of the glares is located in the vicinity of the eye of the user in the captured image.

12. The gaze tracking system of claim 10, wherein the dynamic polarization module is further configured to dynamically polarize the light in a polarization pattern by repeatedly switching between the random polarization phase and the single polarization phase at a rate of 120 Hz.

13. The gaze tracking system of claim 10, wherein the dynamic polarization module is further configured to capture the pupil images and the glint images at a rate of 60 Hz., and detect the gaze locations at a rate of 60 Hz.

14. The gaze tracking system of claim 10, wherein the dynamic polarization module is further configured to:
   detect that the user is not wearing glasses;
   upon detecting that the user is not wearing glasses, refrain from dynamically polarizing the light in the polarization pattern that repeatedly switches between the random polarization phase and the single polarization phase; and
   capture the pupil images and the glint images during the single polarization phases at a rate of 30 Hz or higher.

15. The gaze tracking system of claim 10, wherein the single polarization of the single polarization phases comprises applying the second polarization on the outbound light path.

16. The gaze tracking system of claim 10, wherein the dynamic polarization module is further configured to dynamically polarize the light by alternating a switchable polarizing filter between the first polarization and the second polarization orthogonal to the first polarization.

17. The gaze tracking system of claim 10, wherein the light source is a first light source, wherein the single polarization phase has the single polarization along the reflected light path, and further comprising a second light source that emits unpolarized light to the eyes of the user wearing glasses, wherein the unpolarized light is used to capture the glint images.

18. The gaze tracking system of claim 10, wherein the image capture device is a first image capture device that captures the pupil images, and the dynamic polarization module is further configured to use a second image capture device to capture the glint images.

19. A method for determining gaze locations of an eye of a user, the method comprising:
   shining light along an outbound light path from a light source to the eyes of the user wearing glasses;
   detecting that the user is wearing glasses using an image captured by an image capture device;
   upon detecting that the user is wearing glasses, dynamically polarizing the light in a polarization pattern that repeatedly switches between a random polarization phase and a single polarization phase at a rate of at least 60 Hz, wherein the random polarization phase includes a first polarization of the light along the outbound light path intermediate the light source and the glasses of the user and a second polarization orthogonal to the first polarization along a reflected light path intermediate the glasses and the image capture device, and the single polarization phase having a single polarization along one or more of the outbound light path and the reflected light path;
   during the random polarization phases, filtering out glares reflected from the glasses that would otherwise occlude a pupil of the eye;
   during the random polarization phases when the glares are filtered out, capturing pupil images at a rate of 30 Hz or higher;
   during the single polarization phases, capturing glint images at a rate of 30 Hz or higher;
   repeatedly detecting the gaze locations at a rate of at least 30 Hz based on pupil characteristics identified in the pupil images and glint characteristics identified in the glint images captured proximate in time to the pupil images;
   detecting that the user is not wearing glasses;
   upon detecting that the user is not wearing glasses, refraining from dynamically polarizing the light in the polarization pattern that repeatedly switches between the random polarization phase and the single polarization phase; and
   capturing the pupil images and the glint images during the single polarization phases at a rate of 30 Hz or higher.

20. The method of claim 19, wherein dynamically polarizing the light comprises alternating a switchable polarizing filter between the first polarization and the second polarization orthogonal to the first polarization.

* * * * *